(12) United States Patent
Loewen

(10) Patent No.: US 8,945,059 B2
(45) Date of Patent: Feb. 3, 2015

(54) MEDICAL APPARATUS AND METHOD OF MAKING THE SAME

(71) Applicant: W. L. Gore & Associates, Inc., Newark, DE (US)

(72) Inventor: John L. Loewen, Salt Lake City, UT (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

(21) Appl. No.: 14/062,766

(22) Filed: Oct. 24, 2013

(65) Prior Publication Data

US 2014/0052064 A1 Feb. 20, 2014

Related U.S. Application Data

(63) Continuation of application No. 12/363,252, filed on Jan. 30, 2009, now abandoned.

(51) Int. Cl.
| | | |
|---|---|---|
| *A61M 5/178* | (2006.01) | |
| *A61M 39/06* | (2006.01) | |
| *A61M 39/28* | (2006.01) | |
| *A61M 25/01* | (2006.01) | |
| *F16K 5/10* | (2006.01) | |
| *F16K 31/44* | (2006.01) | |

(52) U.S. Cl.
CPC ....... *A61M 39/0606* (2013.01); *A61M 39/0613* (2013.01); *A61M 39/288* (2013.01); *A61M 25/01* (2013.01); *A61M 2039/062* (2013.01); *A61M 2039/0673* (2013.01)
USPC ............ 604/167.01; 604/165.01; 604/164.01; 604/158; 251/208; 251/248

(58) Field of Classification Search
USPC ............ 604/167.01, 167.03–167.05, 165.01, 604/165.02, 165.04, 158, 159, 164.01, 604/164.02; 251/4, 248, 250.5, 205, 208, 251/212; 74/3.2
See application file for complete search history.

(56) References Cited

U.S. PATENT DOCUMENTS

| | | | | |
|---|---|---|---|---|
| 1,858,352 | A | * | 5/1932 | Young ............................ 251/1.1 |
| 3,329,390 | A | * | 7/1967 | Hulsey ............................ 251/4 |
| 4,307,868 | A | | 12/1981 | Morin |
| 4,540,411 | A | | 9/1985 | Bodicky |
| 5,158,553 | A | * | 10/1992 | Berry et al. ................... 604/248 |
| 5,197,955 | A | | 3/1993 | Stephens et al. |
| 5,211,370 | A | | 5/1993 | Powers |
| 5,256,150 | A | * | 10/1993 | Quiachon et al. ............. 604/171 |
| 5,324,271 | A | | 6/1994 | Abiuso et al. |
| 5,350,363 | A | | 9/1994 | Goode et al. |
| 5,372,350 | A | * | 12/1994 | Kawabe ............................ 251/4 |
| 5,484,418 | A | | 1/1996 | Quiachon et al. |
| 5,779,681 | A | * | 7/1998 | Bonn ........................ 604/167.03 |

(Continued)

FOREIGN PATENT DOCUMENTS

| | | |
|---|---|---|
| EP | 0550069 | 7/1993 |
| EP | 0564578 | 10/1993 |

(Continued)

*Primary Examiner* — Quynh-Nhu H Vu
*Assistant Examiner* — Jenna Zhang
(74) *Attorney, Agent, or Firm* — Gilbert R. Gabo

(57) ABSTRACT

A hemostatic valve apparatus used in medical procedures that provides rapid activation of a sealing mechanism resulting in lower blood loss during use of the sealing device. The valve apparatus incorporates an actuator and two mechanisms that counter-rotate opposite ends of a sealing tube.

19 Claims, 5 Drawing Sheets

(56) References Cited

U.S. PATENT DOCUMENTS

| | | |
|---|---|---|
| 6,276,661 B1 | 8/2001 | Laird |
| 6,610,031 B1 | 8/2003 | Chin |
| 7,172,580 B2 | 2/2007 | Hruska et al. |
| 7,322,556 B2 * | 1/2008 | Bernstein .......................... 251/6 |
| 7,981,086 B2 * | 7/2011 | Focht et al. .............. 604/167.01 |
| 2005/0092944 A1 | 5/2005 | Patterson |
| 2007/0112409 A1 | 5/2007 | Wu et al. |

FOREIGN PATENT DOCUMENTS

| | | |
|---|---|---|
| WO | 01/70308 | 9/2001 |
| WO | 2005/058409 | 6/2005 |

* cited by examiner

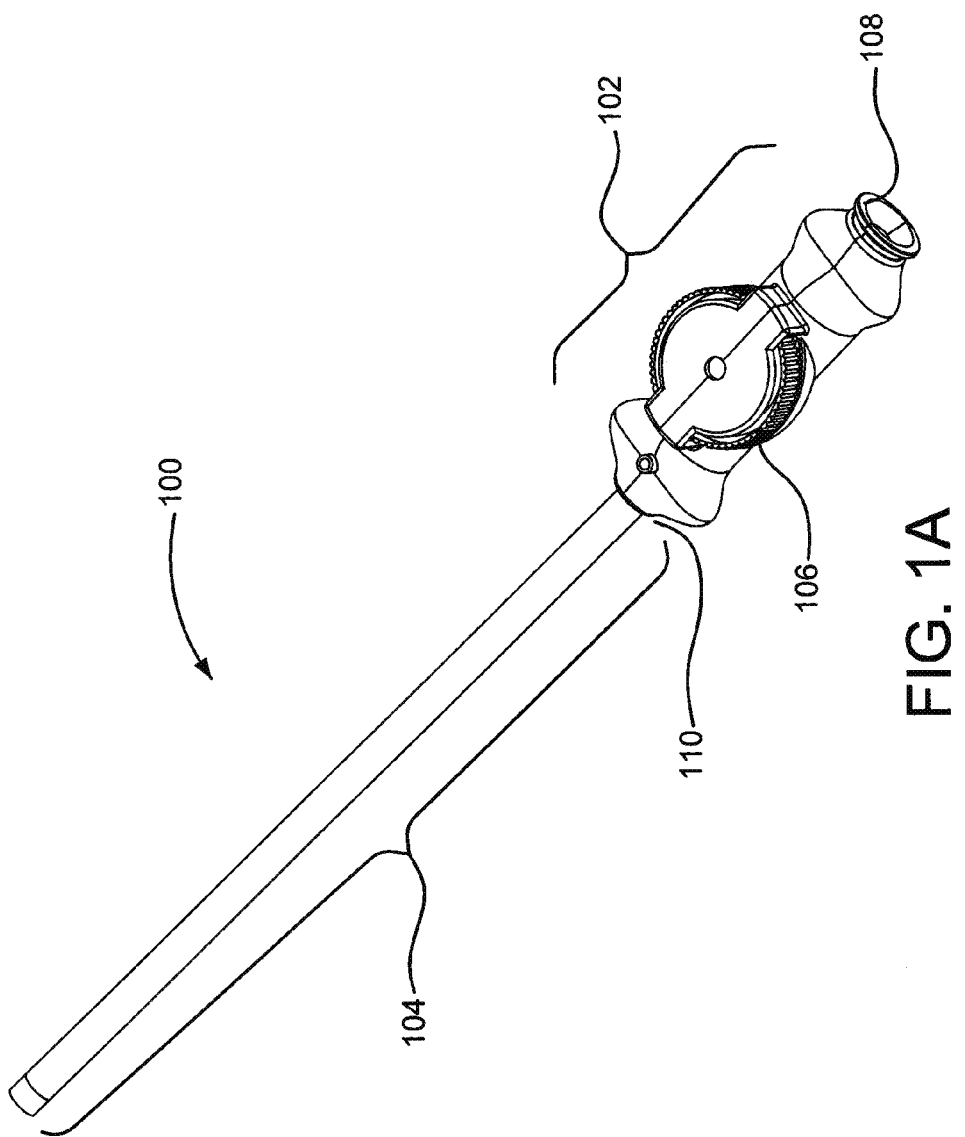

MEDICAL APPARATUS AND METHOD OF MAKING THE SAME

BACKGROUND OF THE INVENTION

1. Field of the Invention

The invention relates to a valve for use in medical applications, more preferably a hemostasis valve apparatus used in medical procedures.

2. Background

Hemostatic valves are used in a wide variety of minimally invasive and conventional surgical procedures. For example, laparoscopic and arthroscopic surgical procedures are often performed through trocar or introducer assemblies which include hemostatic valves. After a trocar or introducer sheath is inserted to provide access to a body target site, surgical instruments, tools, guidewires, implantable devices or diagnostic instruments are inserted into and withdrawn from a hemostatic sealing valve located at a proximal end of the trocar or introducer. The hemostatic valve generally prevents fluid from inadvertently leaving or entering the body target site through the trocar or introducer. As advanced surgical procedures have emerged, hemostatic valves have faced more stringent demands. For example, a wider range of device profiles and a greater number of devices are often passed through a single hemostatic valve.

Current hemostatic valves generally fall into two basic categories: passive and active. To form the desired fluid tight seal, a passive valve generally relies on a resilient sealing body being deformed by the device as it is inserted through the valve. An active valve includes a means to move a sealing body into contact with the traversing device.

A wide variety of active and passive hemostatic valves have been proposed. While these structures have met with varying degrees of success and acceptance, they generally have suffered from common disadvantages. For example sealing bodies (whether passive or active) which seal effectively over a wide range of device cross-sectional profiles tend to impose excess friction on at least some sizes of traversing devices. Active devices which seal effectively over a wide range of device cross-sectional profiles have the disadvantage of requiring extended actuation travel (i.e. thumb or finger motion) along with excessive time to fully open and close the sealing device.

It would be desirable to provide an improved hemostatic valve for use in endovascular, laparoscopic and other surgical procedures. Such a valve should preferably seal over a wide range of device sizes, cross-sectional profiles and lengths without imposing excess friction onto the device. In addition, such a valve should preferably be actuated with a finger or thumb motion and be able to be fully opened or closed in a minimal amount of time and without requiring extended actuation travel.

SUMMARY OF THE INVENTION

Accordingly, the invention comprises a hemostatic valve apparatus used in medical procedures that substantially obviates one or more of the problems due to limitations and disadvantages of the related art.

The instant invention comprises a counter rotating hemostatic valve. In one embodiment, the invention comprises an apparatus comprising a flexible sealing tube, a first mechanism attached to said flexible sealing tube, a second mechanism attached to said flexible sealing tube and an actuator coupled to the first and second mechanisms, wherein the actuator is capable of counter rotating the first and second mechanisms. In another embodiment, said apparatus is a vascular introducer sheath. In another embodiment, said flexible sealing tube has a proximal end, a distal end, and the first rotation mechanism is attached to a distal end of said sealing tube. In another embodiment the first and second mechanisms are attached to opposite ends of said flexible sealing tube. When the first and second mechanisms are counter rotated, said flexible sealing tube is twisted causing said tube to collapse and create a leak proof seal around a device within the tube. It is also contemplated that a leak proof seal can be formed even if no devices are in the flexible sealing tube when the sealing tube is twisted.

The invention also comprises a valve for effecting selective closure of a catheter lumen to control fluid flow through said catheter lumen, comprising, a flexible sealing tube having a lumen extending from a proximal end to a distal end, a first rotation mechanism attached to the tube, wherein the first rotation mechanism comprises a first gear, a second rotation mechanism attached to the flexible sealing tube, wherein the second rotation mechanism comprises a second gear, and an actuator coupled to the first and second rotation mechanisms, wherein the actuator is capable of counter rotating the first and second rotation mechanisms.

An advantage of the present invention is to provide faster activation of the sealing mechanism. Other advantages of the present invention are to provide lower blood loss during the activation of the sealing device and to provide an intuitive and easy to use activation mechanism.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings:

FIG. 1A is a perspective view of a hemostatic valve assembly according to a configuration of the present invention.

DETAILED DESCRIPTION OF THE ILLUSTRATED EMBODIMENTS

Figure 1B:
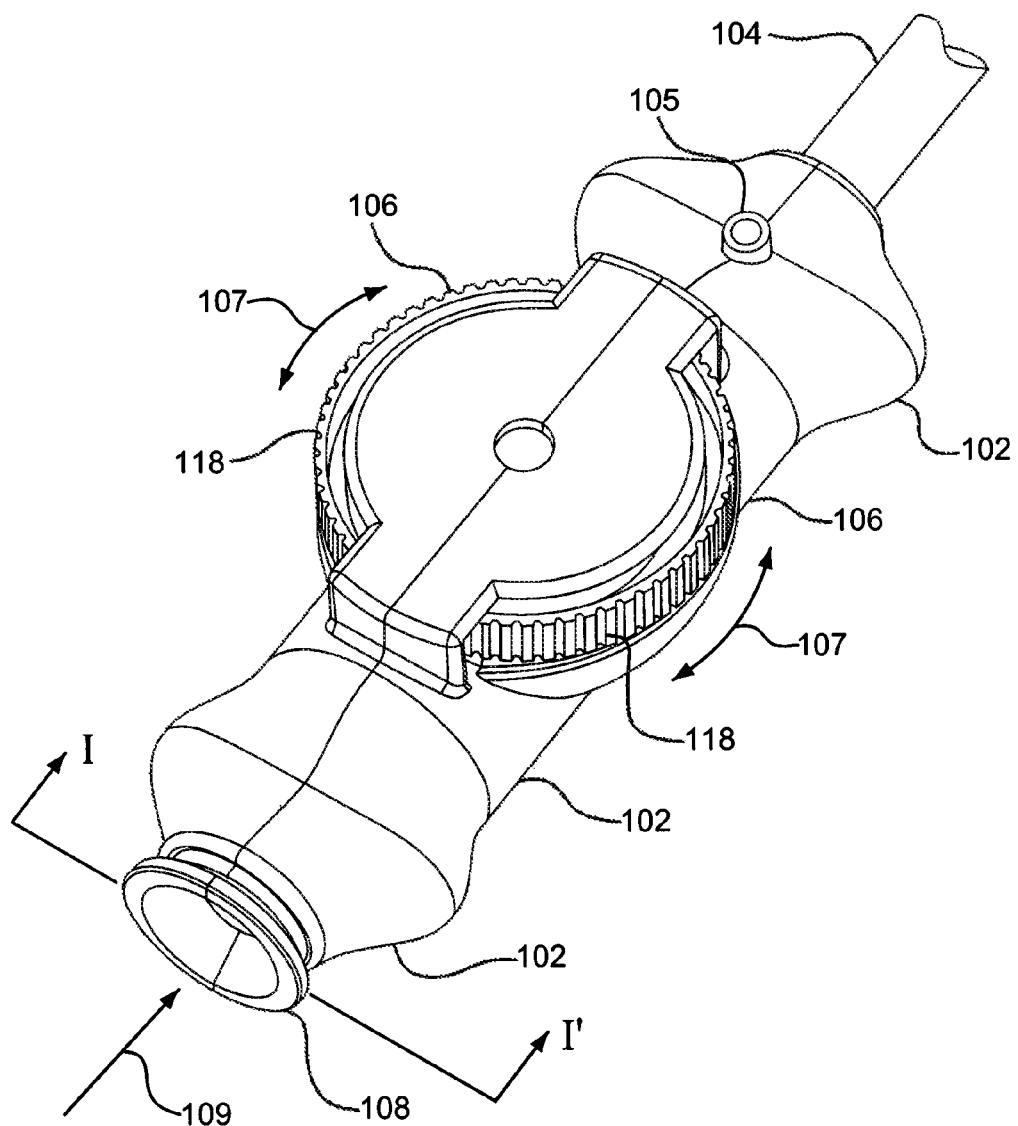
FIG. 1B is a magnified perspective view of the housing previously shown in FIG. 1A.

The invention relates to a valve apparatus for use in medical applications, more preferably a hemostatic valve apparatus used in medical procedures. The medical procedures may be a laparoscopic, endoscopic, and other medical procedures.

Reference will now be made in detail to an embodiment of the present invention, examples of which are illustrated in the accompanying drawings.

Referring to FIG. 1A, an apparatus according to an embodiment of the invention is generally depicted as reference number 100. The apparatus 100 includes a housing 102 and a sheath 104 connected to the housing 102. Sheath 104 may be manufactured of either fluorinated ethylene propylene (FEP) or extruded high density polyethylene or any other material with suitable biocompatible and mechanical properties. One of skill in the art can readily appreciate that there are a wide variety of potential materials that can be used to facilitate the present invention. Sheath 104 may be of any size. In one embodiment, sheath 104 is from about 12 to about 26 Fr. The proximal most end of the sheath 104 may comprise a flange that will keep sheath 104 from sliding longitudinally within housing 102 (105 FIG. 1D). Sheath 104 may be attached to housing 102 in a variety of ways. In one embodiment, sheath 104 may be attached to the housing 102 by using adhesives such as polyurethane adhesives, quick setting cyanoacrylate adhesives or ultraviolet cure adhesives. In another embodiment, sheath 104 is attached to housing 102 by ultrasonic welding, interference fit, thermal bond, insert molding or a combination thereof. One of skill in the art can readily appreciate that there are a wide variety of potential means for attaching sheath 104 to housing 102. Said attachment of sheath 104 to housing 102 will create a leak proof attachment. For the purposes of this invention, the terms "leak proof attachment" and "leak proof seal" means that either no fluids or an insignificant amount of fluids will leak from said attachment or seal when used in surgical or interventional procedures.

Housing 102 may be of an ergonomic design to facilitate use. An actuator 106 is partially covered with housing 102. Housing 102 includes a proximal end 108 and distal end 110. The proximal end 108 is configured to include a proximal valve (not shown). Housing 102 can be constructed out of polymethyl methacrylate (PMMA or Acrylic), polystyrene (PS), acrylonitrile butadiene styrene (ABS), polyvinyl chloride (PVC), modified polyethylene terephthalate glycol (PETG), cellulose acetate butyrate (CAB), polyethylene (PE), high density polyethylene (HDPE), low density polyethylene (LDPE or LLDPE), polypropylene (PP), polycarbonate (PC), modified polyphenylene oxide (Mod PPO), polyphenelyne ether (PPE), thermoplastic polyurethane (TPU), polyamide (PA or Nylon), polyoxymethylene (POM or Acetal), polyethylene terephthalate (PET, Thermoplastic Polyester), polybutylene terephthalate (PBT, thermoplastic polyester), ultra high molecular weight polyethylene (UHMW-PE), fluorinated ethylene propylene (FEP), or any other medical grade polymer commonly known in the art.

In another embodiment, housing 102 is comprised of two halves that are joined together to form housing 102 and may enclose a number of components, as described below. Said two halves of housing 102 can be joined together by adhesives, any method described above or method known in the art.

FIG. 1B depicts a perspective view of the housing 102 shown in FIG. 1A. In one embodiment, housing can be configured to allow a user to grasp said housing with one hand. Portions of actuator 106 are exposed through an opening in the housing allowing the user to rotate the actuator 106 in the directions shown by arrows 107. In one embodiment, the actuator can be rotated about 180° or less. In another embodiment, the actuator can be rotated to a maximum of about 360°. Internal to the housing are two mechanisms that are driven by the rotation of the actuator. The two mechanisms are attached to opposite ends of a flexible sealing tube (as described below). Rotation of the actuator 106 causes the two mechanisms to "counter rotate" and twist the sealing tube ends in opposite directions. The twisting of the sealing tube causes the tube to collapse around a device that is inserted into the housing, in the direction as indicated by arrow 109, to create a leak proof seal. In one embodiment, said actuator is attached to said first and second mechanism via a gear. Said gear can be selected from the group consisting of a spur gear, helical gear, bevel gear, worm gear, and combinations thereof. Shown in FIG. 1B is an optional ergonomic user interface feature 118 located along at least a portion of the actuator 106 outer surface. Ergonomic feature 118 can help user grip actuator 106 for easy turning. In one embodiment, said actuator can be turned using operator's hand. In another embodiment, said actuator can be turned using only a thumb or a thumb and forefinger. Once the leak proof seal is made, the medical apparatus or actuator may have a means of keeping said actuator in place to maintain said leak proof seal. In one embodiment, said means is a latch. Other means include spring loaded detents, locking screws, locking cams or frictional interference fits.

Also shown in FIG. 1B is an optional flushing port 105. The function and use of flushing port 105 and fitting are commonly known in the art.

Figure 1C:
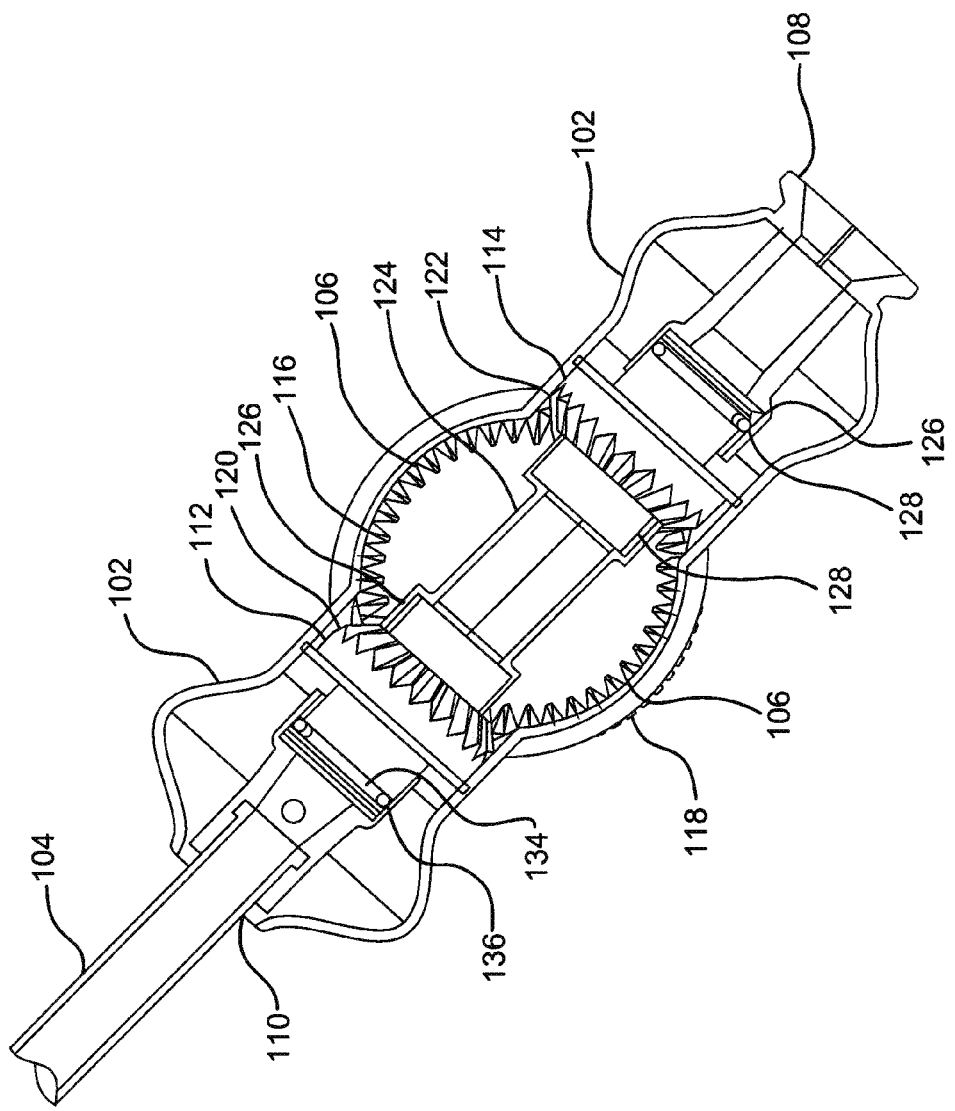
FIG. 1C is a perspective cut-away view of a valve mechanism according to a configuration of the present invention.

FIG. 1C illustrates a cross-sectional view of FIG. 1B along line I to I'.

The actuator 106 is used to rotate a first mechanism 112 and counter rotate a second mechanism 114. In one embodiment, the actuator 106 includes a beveled gear portion 116 on at least a portion of its circumference and an optional ergonomic user interface feature 118. The first mechanism includes a beveled gear portion 120 and the second mechanism includes a beveled gear portion 122 on their respective circumferences. The first mechanism is attached to a distal portion of flexible sealing tube 124 with a coupling agent and the second mechanism is attached to a proximal portion of flexible sealing tube 124 with another coupling agent to make a leak proof attachment. In another embodiment, the first mechanism 112 includes a sealing channel 134 for receiving sealing mechanism 136. The second mechanism 114 also includes a sealing channel 126 for receiving sealing mechanism 128. Sealing mechanisms (128 and 136) can be selected from the group consisting of O-rings, flexible knife-edge seals, viscous gels or any other system known in the art. Sealing mechanisms (128 and 136) provide a rotatable fluid seal between the first/second mechanisms 112, 114 and the housing 102.

Figure 1D:
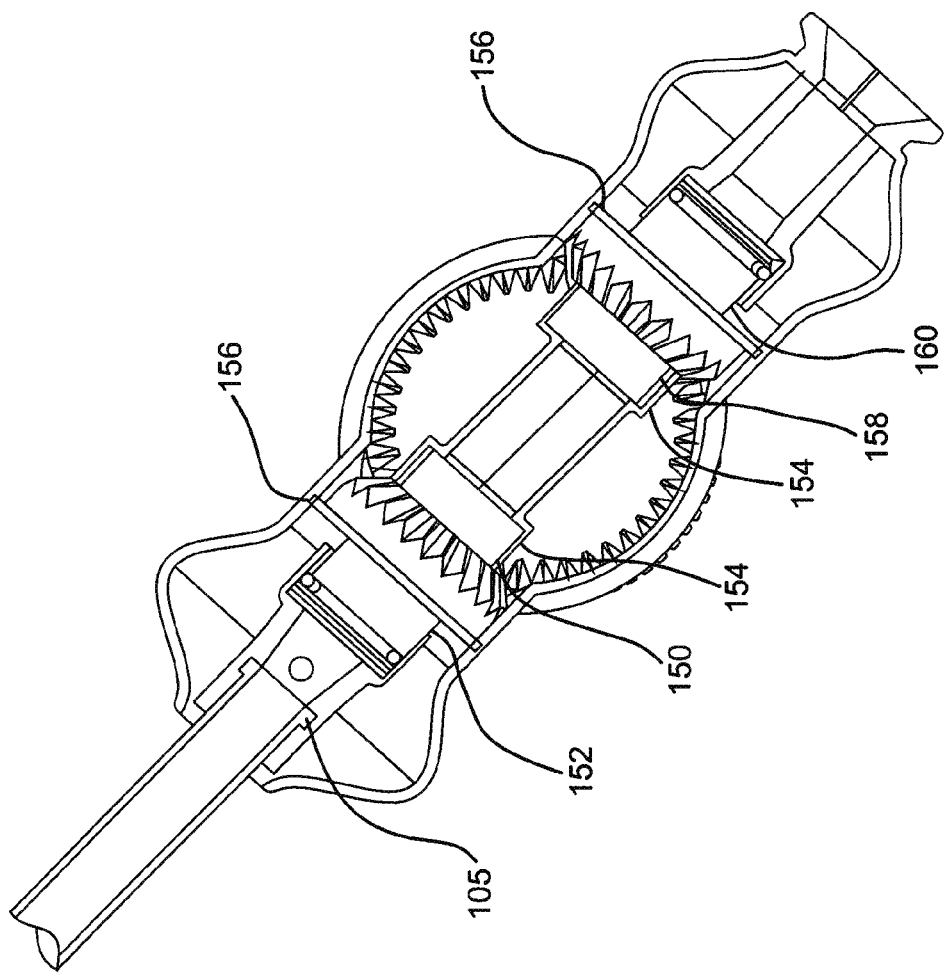
FIG. 1D is a perspective cut-away view of a valve mechanism according to a configuration of the present invention.

In another embodiment, as depicted in FIGS. 1C and 1D, mechanism 112 is a solid piece that comprises proximal shoulder 150, a distal shoulder 152, beveled gear portion 120 on at least a portion of its circumference and a lumen in the center of said mechanism so that medical tools, such as, catheters, sheaths, guidewires, and the like, used in medical procedures can pass through mechanism 112. Mechanism 112 can be constructed out of any biocompatible metal or plastic with suitable biocompatible and mechanical properties. For example polymethyl methacrylate (PMMA or Acrylic), polystyrene (PS), acrylonitrile butadiene styrene (ABS), polyvinyl chloride (PVC), modified polyethylene terephthalate glycol (PETG), cellulose acetate butyrate (CAB), polyethylene (PE), high density polyethylene (HDPE), low density polyethylene (LDPE or LLDPE), polypropylene (PP), polycarbonate (PC), modified polyphenylene oxide (Mod PPO), polyphenelyne ether (PPE), thermoplastic polyurethane (TPU), polyamide (PA or Nylon), polyoxymethylene (POM or Acetal), polyethylene terephthalate (PET, Thermoplastic Polyester), polybutylene terephthalate (PBT, Thermoplastic Polyester), ultra high molecular weight polyethylene (UHMW-PE), fluorinated ethylene propylene (FEP), or any other medical grade polymer as commonly known in the art can be used to fabricate mechanism 112 or other components of the apparatus 100.

Proximal shoulder 150 is designed to accept sleeve 154 of the flexible sealing tube 124 to create a leak proof attachment. The sleeve 154 can be attached by a mechanical coupling agent, such as a collar, crimp ring, snap ring, clamp, combinations thereof, or methods known in the art. In another embodiment, sleeve 154 can be attached by insert molding or by a biocompatible adhesive, such as a silicone adhesive, urethane adhesive, cyanoacrylate adhesive, epoxy adhesive or combinations thereof, or other methods known in the art. Mechanism 112 also comprises distal shoulder 152. Distal shoulder 152 may comprise a sealing channel 134 for receiving a rotatable seal (or other sealing mechanisms) 136. Said rotatable seal can be an O-ring. Other sealing mechanisms comprise flexible knife-edge seals, viscous gels and the like. These mechanisms can be used to form rotatable seals. Said apparatus can further comprise another sealing mechanism, e.g., elastic diaphragm, compression fitting, cap, second tube, brushes, inflatable valve, etc.

In one embodiment, distal shoulder 152 will be placed in a cradle molded into housing 102. Once the sealing mechanism 136 and sleeve are placed in housing 102, a leak proof attachment, that allows rotation of mechanism 112, will be formed when housing 102 is assembled. Mechanism 112 may also comprise at least one flange 156, which, in one embodiment, prevents mechanism 112 from sliding longitudinally in housing 102 and will allow rotation of mechanism 112.

Similarly, mechanism 114 comprises proximal shoulder 160, a distal shoulder 158 and beveled gear portion 122 on at least a portion of its circumference. Proximal shoulder 158 will accept sleeve 154 of the flexible sealing tube 124 to create a leak proof attachment. Sleeve 154 is attached to shoulder 158 as described above. Further, mechanism 114 comprises proximal shoulder 160 which may comprise a sealing channel 126 for receiving sealing mechanism 128. Said sealing mechanism can be an O-ring or any type of sealing mechanism described above. In one embodiment, proximal shoulder 160 will be placed in a cradle molded into housing 102. Once the sealing mechanism 128 and sleeve are placed in housing 102 a leak proof attachment, that allows rotation of mechanism 114, will be formed when housing 102 is assembled. Mechanism 114 may also comprise at least one flange 156, which, in one embodiment, prevents mechanism 114 from sliding longitudinally in housing 102 and allows rotation of mechanism 114.

The flexible sealing tube 128 is a conduit for passing medical tools (devices), such as, catheters, sheaths, guidewires, and the like, used in medical procedures. Preferably, the tube is at least a partially compressible conduit that enables a fluid seal around a passed device. The tube may be designed to have any number of different geometrically shaped cross-sections, such as circular, oval, elliptical, diamond, square, polygon, combinations thereof and the like. In addition, the sleeve may narrow along its length, e.g., having a conical shape. For example, a cross-section near the sleeve may be larger than a cross-section at the other end of the tube. Preferably, the tube is designed to have a circular cross-section. In addition, the tube may include localized regions of restricted or enlarged cross-sections.

When utilizing a circular cross-section, the inside diameter of the untwisted tube may be in the range from about 1 mm to about 30 mm or more. In one embodiment, the inside diameter ranges from about 4 mm to about 26 mm. In another embodiment, the inside diameter ranges from about 4 mm to about 8 mm.

Depending on the material used, the wall thickness of the flexible sealing tube will depend on the tensile strength of material and ease of twisting. A person of skill in the art can readily determine the required wall thickness for an application. In one embodiment, the wall thickness of said flexible sealing tube is from about 0.5 mm to about 2 mm.

The length of the flexible sealing tube may vary according to the application. In one embodiment, the length of said flexible sealing tube is from 0.5 cm to about 30 cm. In another embodiment, the length of said flexible sealing tube is from about 6 cm to about 25 cm. In another embodiment, the length of said flexible sealing tube is from about 2 cm to about 10 cm. A person of skill in the art can readily determine the required length for specific applications.

The flexible sealing tube 124 can be constructed, in whole or in part, utilizing a variety of materials, such as, synthetic materials, natural materials, and combinations thereof. In one embodiment, the flexible sealing tube can be constructed of an elastic polymer such as silicone, polyurethane, latex or the like. Other suitable tube materials include expanded polytetrafluoroethelene (ePTFE), silks, polyester weaves or other medical grade materials. Porous materials can be rendered less pervious to fluids by filling the tube material voids with an elastomer or other filling agents. The flexible sealing tube can further incorporate reinforcement materials or members such as high strength fibers or ribbons. The flexible sealing tube can also be fabricated from two or more different materials having different mechanical properties such as durometers or degrees of elasticity.

One embodiment of the invention comprises a sealing tube made with at least two types of material. For the purposes of this invention, different types of materials can be made from the same substance(s) but have different properties, for example, different durometer or elasticity. Thus, in one embodiment, the flexible sealing tube has a low durometer inner material combined with a higher durometer outer material. For example a tube can comprise at least two materials having a difference in durometers of about 10%, about 20%, about 30%, about 40%, about 50% or more. The low durometer inner material can more readily conform to an irregular shape and thus facilitate sealing around an inserted device. The higher durometer outer material can support the inner low durometer material and enhance the tear resistance of said tube. The high durometer material can also increase the compressive force imparted onto the device being inserted into a tube. The difference in durometer can be attributed to a flexible sealing tube made with two different materials or with the same material but is made to have differing durometer, for example by varying the thickness of the material.

The flexible sealing tube 124 can also have a difference in durometers along the length of the tube. For example the tube may have a low durometer on one or both ends, combined with a higher durometer portion in the mid-section of the tube. The tube can also be configured in the opposite form with a higher durometer on an end (or ends) of the flexible sealing tube, with a lower durometer portion in the mid-section of the tube. The difference in durometers can be about 10%, about 20%, about 30%, about 40%, about 50% or more.

The flexible sealing tube 124 can also have a varying wall thickness. For example the tube can have a thick wall at the end (or ends) of the tube combined with a thinner wall in the mid-section of the tube. The tube can also be configured in the opposite form with a thin wall on the end (or ends) with a thicker wall in the mid-section. The tube wall thickness can also be "tapered" with a progressive change in wall thickness along the length of the tube. The difference in wall thickness along the length of a tube can be about 10%, about 20%, about 30%, about 40%, about 50% or more. Combinations of varied durometers, varied materials and various wall thicknesses can be incorporated into the flexible sealing tube. Tubes can also have "repeating structures" or repeating segments joined together. For example the properties of a tube can vary along the length of a segment and multiple segments can be joined to form a tube.

The flexible sealing tube can also be "pre-compressed" during assembly of the valve mechanism. For example a tube having a free, unconstrained length of about 4 cm can have a pre-compressed length of about 3 cm after being assembled into a valve mechanism. Pre-compressing the tube reduces the tube's wall tension as the tube is twisted. Less tension in the tube wall increases the conformability of the tube, resulting in enhanced sealing around a device. The difference between a free unconstrained tube length and a pre-compressed tube length can be about 3%, about 5%, about 7%, about 10%, about 15%, about 20%, about 25%, about 30% or more.

To aid in the insertion of a medical device into the sealing tube, a lubricious material, coating or liner may be incorporated onto the inner diameter of the tube as commonly known in the art. In addition anti-microbial and/or therapeutic agents can be applied to the sealing tube.

Another embodiment of the invention comprises a valve apparatus, wherein the valve apparatus comprises: a flexible sealing tube; a first mechanism attached to flexible sealing tube; a second mechanism attached to flexible sealing tube; and an actuator coupled to the first and second mechanisms, wherein the actuator is capable of counter rotating the first and second mechanisms (112 and 114, respectively). In one embodiment, said valve apparatus is a component of a medical device apparatus. In another embodiment, said medical device apparatus is a vascular introducer sheath or any device that allows access to a patient's vasculature. Vascular introducer sheaths are well known components of vascular access systems which are used in a wide variety of diagnostic and therapeutic vascular procedures, such as angiography, angioplasty, thermolysis, and embolization procedures. Vascular access systems typically include an introducer sheath for use in combination with a guide wire and a dilator. One important feature of said valve is that it prevents bodily fluids from escaping through the valve when an introducer sheath is inserted into a patient's vasculature. Another feature is that when medical tools (devices), such as, catheters, sheaths, guidewires, and the like, used in medical procedures, are inserted into said valve and then closed, as described above, a leak proof seal will be made, thus preventing bodily fluids from leaving the patient's vasculature or allowing an insignificant amount of bodily fluids from leaving the patient's vasculature.

Reference will now be made in detail to an embodiment of the present invention, example of which is illustrated in the accompanying drawing, FIG. 2.

Figure 2:
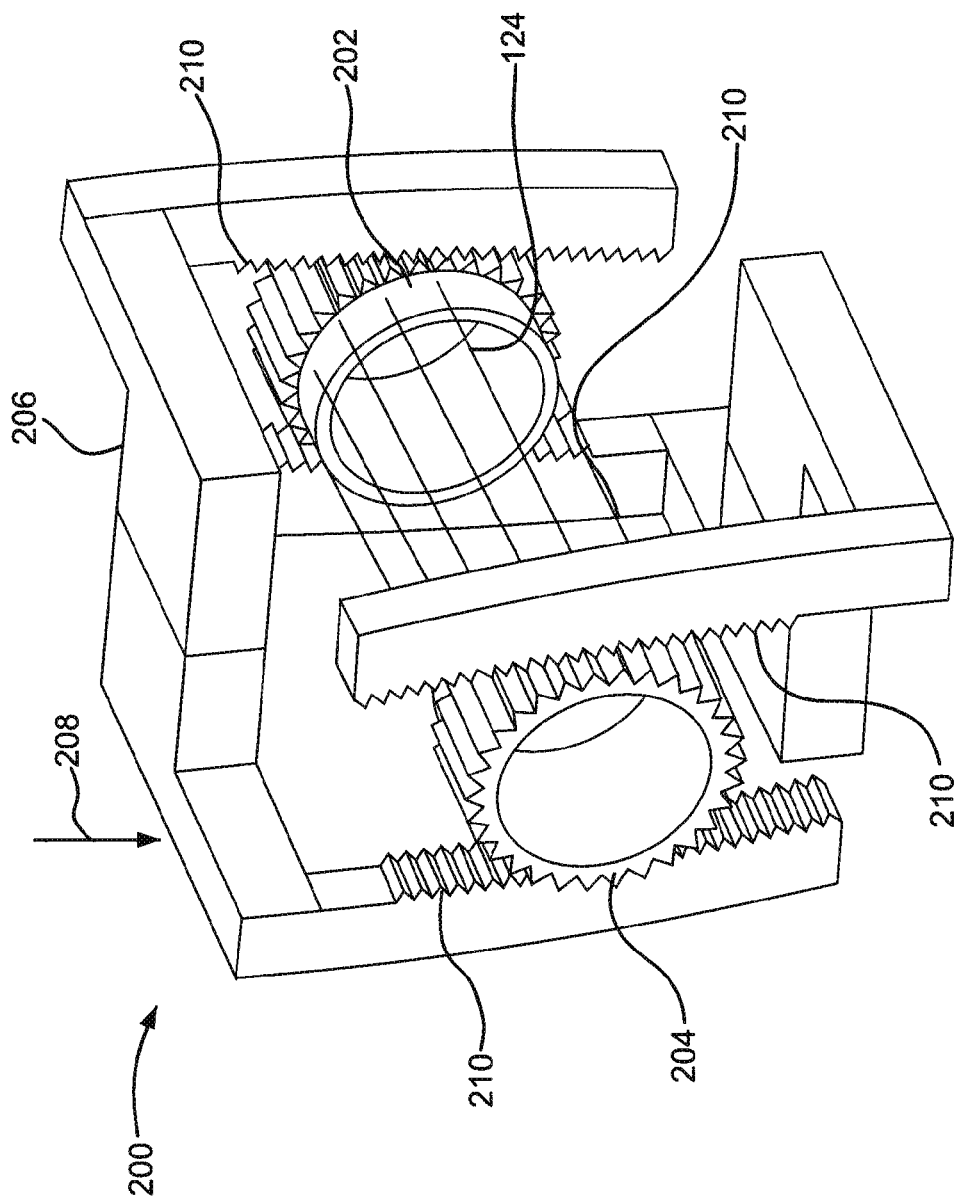
FIG. 2 is a perspective view of an alternate actuation mechanism suitable for use as a valve mechanism.

FIG. 2 illustrates an alternate valve mechanism 200 according to another embodiment of the invention. The mechanism shown in FIG. 2 can be contained with a suitable housing (not shown) similar to that shown in FIGS. 1A and 1B. Referring to FIG. 2, a distal end of tube 124 is attached to a first mechanism 202, and the proximal end of tube 124 is attached to second mechanism 204. When actuator 206 is moved in the direction as depicted by arrow 208, the first and second mechanisms (202, 204) are driven by the linear track gears 210. The mating gear teeth cause the first and second mechanisms (202, 204) to counter rotate, causing the tube 124 to twist and compress upon itself or to compress upon a device within the tube. Said actuator can be moved by operator's hand, by a clamp or other methods known in the art.

This invention is further illustrated by the following examples which should not be construed as limiting. The contents of all the Figures are incorporated herein by reference.

Example 1

A hemostatic valve assembly similar to FIG. 1 was manufactured using the following components and assembly process:

1) Components were fabricated using a rapid prototyping, stereolithography (SLA) process. The parts were fabricated by ProtoCam (Northampton, Pa.) using an SLA material designated as Accura® 25 plastic. This material when cured had an advertised tensile strength of about 38 Mpa, a tensile modulus of about 1590-1660 Mpa, an elongation to break of about 13-20% and a hardness of about 80 Shore D. The tensile and elongation data were derived using test method ASTM D 638. Seven parts were fabricated using this SLA process and Accura® 25 plastic material. The parts included a top housing, bottom housing, an actuation or wheel bevel gear, two identical bevel gear seals, a proximal hub and a distal hub.

2) Other materials required for the assembly of the hemostatic valve were purchased items. An elastomeric tube (used for the twist sealing component) having a outer diameter of about 0.4" (1 cm), a wall thickness of about 0.03" (0.8 mm) and a length of about 1.3" (3.3 cm) was procured from Specialty Silicone Fabricators (Paso Robles, Calif.). This tube was formed of an elastomeric silicone having a durometer of about 30A. Two O-rings (used for seals), size –014 of 70A silicone were procured from Molding Solutions (Lexington, Ky.). A polycarbonate dowel pin (used as an actuation wheel shaft) having a diameter of about 0.25" (6.4 mm) and a length of about 0.3" (7.6 mm) was supplied from in-house stock. An RTV silicone adhesive and a quick set cyanoacrylate adhesive were supplied from in-house stock.

3) The hemostatic valve was then assembled using the components described above. The polycarbonate dowel pin was glued into the center hole of the actuation bevel gear using the quick set cyanoacrylate adhesive. This gear with attached dowel pin was then placed into the bottom housing. The ends of the elastomeric silicone tube were then glued to the two bevel gear seals using the RTV silicone adhesive. The two O-rings were then placed over the ends of the two bevel gear seals. The proximal and distal hubs were then placed over the ends of the bevel gear seals. The silicone tube with attached bevel gear seals, O-rings and proximal and distal hubs were then placed onto the actuation bevel gear and into the slots formed into the bottom housing. The top housing was then placed onto the bottom housing. The top and bottom housings were then secured together with the quick set cyanoacrylate adhesive, forming a hemostatic valve assembly as depicted in FIG. 1.

4) An optional extended sheath can be added to the distal end of the valve assembly along with an optional bleed tube and valve.

Example 2

The hemostatic valve assembly of EXAMPLE 1 was evaluated to determine the amount of thumb motion required to fully open the valve starting from a fully closed state. For a total thumb motion that extended over a 1.3" length, the sealing element traversed from a fully closed state to a fully opened state having an inner diameter of about 0.34". By comparison an identical tube twisted from only one end should require about two times the amount of thumb motion.

It will be apparent to those skilled in the art that various modifications and variation can be made in the present invention without departing from the spirit or scope of the invention. Thus, it is intended that the present invention cover the modifications and variations of this invention provided they come within the scope of the appended claims and their equivalents.

What is claimed is:

1. A vascular introducer sheath assembly for endoluminal delivery of medical treatment, said vascular introducer sheath assembly comprising:
   a catheter and a valve coupled to the catheter for controlling fluid flow through the catheter, each of the catheter and the valve being configured to accommodate delivery of the medical device therethrough, the valve having:
      a valve housing having a proximal opening and an opposite distal opening, the distal opening being in fluid communication with the catheter,
      a flexible tube having a proximal end and an opposite distal end, the tube having a longitudinal axis extending along the proximal and distal ends of the tube, the tube having a lumen extending along the longitudinal axis between the proximal and distal ends of the tube, the proximal and distal ends of the tube being in fluid communication with the proximal and distal openings of the housing, respectively, such that in an open configuration the tube allows fluid to pass between the proximal and distal openings of the housing via the lumen,
      a first gear having an axis of rotation aligned to the tube longitudinal axis and fixedly secured to the distal end of the tube,
      a second gear having an axis of rotation aligned to the tube longitudinal axis and fixedly secured to the proximal end of the tube, and
      an actuator having a third gear rotatably coupled to the housing for rotation about a third gear axis, the third gear being directly engaged with each of the first and second gears so as to cause a collapsing of the lumen by rotation of the proximal and distal ends of the tube in opposite directions in response to selective rotation of the third gear about the third gear axis.

2. The vascular introducer sheath assembly of claim 1, wherein the third gear axis of rotation is orthogonal to the longitudinal axis.

3. The vascular introducer sheath assembly of claim 1, wherein the tube comprises a material selected from the group consisting of expanded polytetrafluoroethelene (ePTFE), silks, polyester weaves.

4. The vascular introducer sheath assembly of claim 1, wherein proximal and distal ends of the tube can be counter rotated by selective rotation of the third gear to substantially close the lumen.

5. The vascular introducer sheath assembly of claim 1, wherein the proximal and distal ends of the tube can be counter rotated by selective rotation of the third gear to collapse the lumen and thereby form a seal between the tube and a medical device extending through the lumen of the tube.

6. The vascular introducer sheath assembly of claim 5, wherein the medical device is selected from the group consisting of catheters, sheaths, diagnostic instruments, surgical instruments, cannulas, and guidewires.

7. The vascular introducer sheath assembly of claim 1 further comprising a latch for releasably locking the actuator in place.

8. The vascular introducer sheath assembly of claim 1, wherein the tube has a substantial circular cross section.

9. The vascular introducer sheath assembly of claim 1, wherein the tube has a polygon cross section.

10. The vascular introducer sheath assembly of claim 1, wherein the tube has an inner diameter of at least 3 mm.

11. The vascular introducer sheath assembly of claim 1, wherein the tube comprises two or more different materials.

12. The vascular introducer sheath assembly of claim 1 further comprising an additional sealing mechanism selected from the group consisting of an elastic diaphragm, a compression fitting, a cap, a second tube, brushes, and an inflatable valve.

13. The vascular introducer sheath assembly of claim 1, wherein the tube has a length in the range from about 6 to about 25 mm.

14. The vascular introducer sheath assembly of claim 1, wherein the actuator can be rotated about 180° or more.

15. The vascular introducer sheath assembly of claim 1, wherein the actuator can be rotated to a maximum of about 360°.

16. The vascular introducer sheath assembly of claim 1, further comprising a radiopaque marker.

17. A medical device kit, comprising:
   a vascular introducer sheath assembly according to claim 1; and
   a tissue dilator.

18. A medical device kit, comprising:
   a medical device;
   a vascular introducer sheath assembly for endoluminal delivery of medical treatment, said vascular introducer sheath assembly comprising:
      a catheter and a valve coupled to the catheter for controlling fluid flow through the catheter, each of the catheter and the valve being configured to accommodate delivery of the medical device therethrough, the valve having:
         a valve housing having a proximal opening and an opposite distal opening, the distal opening being in fluid communication with the catheter,
         a flexible tube having a proximal end and an opposite distal end, the tube having a longitudinal axis extending along the proximal and distal ends of the tube, the tube having a lumen extending along the longitudinal axis between the proximal and distal ends of the tube, the proximal and distal ends of the tube being in fluid communication with the proximal and distal openings of the housing, respectively, such that in an open configuration the tube allows fluid to pass between the proximal and distal openings of the housing via the lumen,
         a first gear having an axis of rotation aligned to the tube longitudinal axis and fixedly secured to the distal end of the tube,
         a second gear having an axis of rotation aligned to the tube longitudinal axis and fixedly secured to the proximal end of the tube, and
         an actuator having a third gear rotatably coupled to the housing for rotation about a third gear axis, the third gear being directly engaged with each of the first and second gears so as to cause a collapsing of the lumen by rotation of the proximal and distal ends of the tube in opposite directions in response to selective rotation of the third gear about the third gear axis.

19. The medical device kit of claim 18, wherein the medical device is selected from the group consisting of catheters, sheaths, diagnostic instruments, surgical instruments, cannulas, and guidewires.

* * * * *